(12) United States Patent  (10) Patent No.: US 9,237,896 B2
McGhie  (45) Date of Patent: Jan. 19, 2016

(54) GHOST RING GUIDE FOR ASSISTANCE IN PERCUTANEOUS INSERTIONS

(71) Applicant: Cook Medical Technologies LLC, Bloomington, IN (US)

(72) Inventor: Thomas W. McGhie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 201 days.

(21) Appl. No.: 13/657,107

(22) Filed: Oct. 22, 2012

(65) Prior Publication Data

US 2013/0103036 A1   Apr. 25, 2013

Related U.S. Application Data

(60) Provisional application No. 61/549,961, filed on Oct. 21, 2011.

(51) Int. Cl.
*A61B 17/58* (2006.01)
*A61B 17/60* (2006.01)
*A61F 2/00* (2006.01)
*A61B 17/17* (2006.01)
*A61B 17/70* (2006.01)
*A61B 19/00* (2006.01)

(52) U.S. Cl.
CPC ......... *A61B 17/1757* (2013.01); *A61B 17/7094* (2013.01); *A61B 2019/5466* (2013.01)

(58) Field of Classification Search
CPC ..................... A61B 17/1757; A61B 17/3403
USPC ............................................... 606/96
See application file for complete search history.

(56) References Cited

U.S. PATENT DOCUMENTS

| 3,941,127 | A | 3/1976 | Froning |
| 3,955,558 | A | 5/1976 | Fuisz |
| 4,638,799 | A | 1/1987 | Moore |
| 5,138,914 | A * | 8/1992 | Brickner ................. 81/451 |
| 5,641,287 | A | 6/1997 | Gittleman |
| 6,375,659 | B1 | 4/2002 | Erbe et al. |
| 6,551,836 | B1 | 4/2003 | Chow et al. |
| 7,153,307 | B2 | 12/2006 | Scribner et al. |
| 7,601,157 | B2 | 10/2009 | Boyd et al. |
| 7,708,742 | B2 | 5/2010 | Scribner et al. |
| 7,731,720 | B2 | 6/2010 | Sand et al. |
| 7,771,431 | B2 | 8/2010 | Scribner et al. |
| 7,914,537 | B2 | 3/2011 | Boyd et al. |
| 7,972,340 | B2 | 7/2011 | Sand et al. |
| 8,409,211 | B2 | 4/2013 | Baroud |
| 2010/0191259 | A1 * | 7/2010 | Suzuki ............... A61B 17/0482 606/144 |
| 2010/0262200 | A1 * | 10/2010 | Ray et al. .................. 606/86 A |

* cited by examiner

*Primary Examiner* — David Bates
*Assistant Examiner* — Olivia C Chang
(74) *Attorney, Agent, or Firm* — Woodard, Emhardt, Moriarty, McNett & Henry LLP

(57) ABSTRACT

Among other things, there is disclosed embodiments of devices for assisting in aiming and inserting percutaneous medical tools or devices. A mandrel portion with a sharpened end has two or more guiding or directing members attached to it. The guiding or directing members at least partially define spaces that form part of a channel that is oriented parallel to the longitudinal axis of the mandrel portion, and one or both can be easily visualizable using imaging technology. The clinician can insert the aiming or guiding device into the patient, use imaging technology along the axis of the channel of the device to see whether the device is accurately placed, and if so, the guiding or directing members can be used to guide the percutaneous insertion of a medical tool or device.

20 Claims, 3 Drawing Sheets

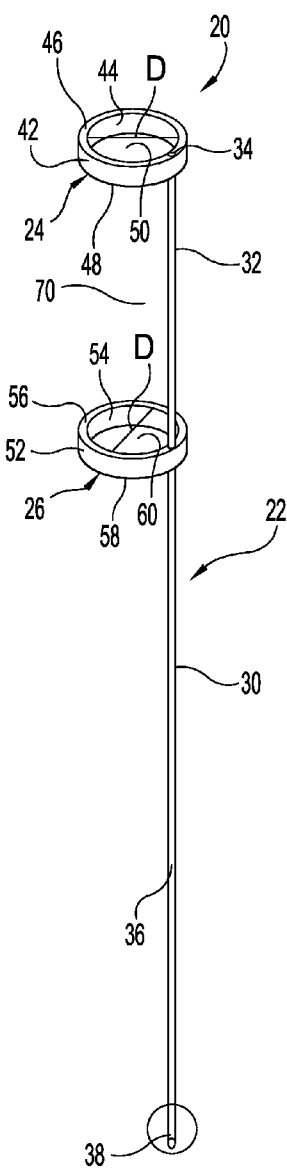
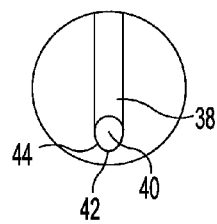
Fig. 1
Fig. 1A
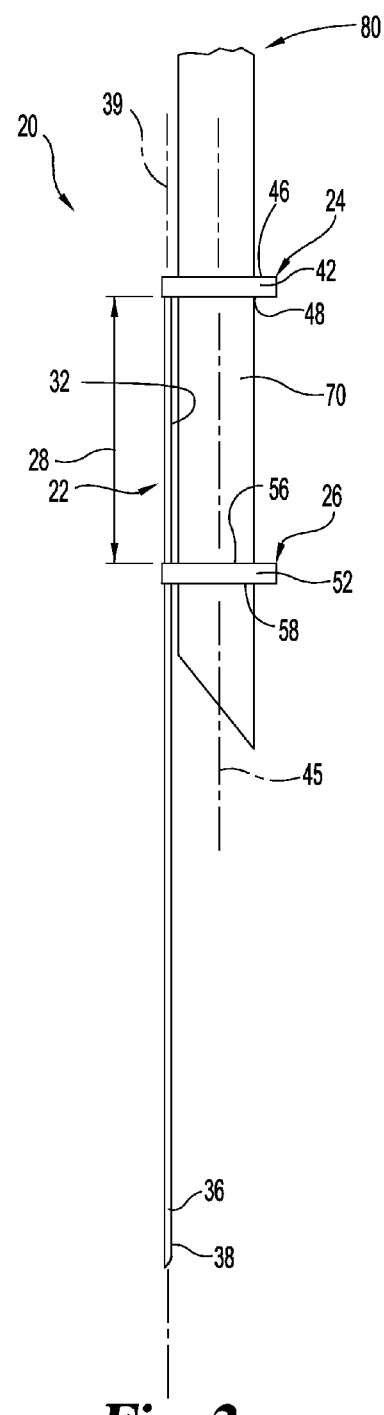
Fig. 2

GHOST RING GUIDE FOR ASSISTANCE IN PERCUTANEOUS INSERTIONS

REFERENCE TO RELATED APPLICATIONS

This application claims the benefit of U.S. Provisional Patent Application No. 61/549,961, filed Oct. 21, 2012, which is hereby incorporated by reference.

The present disclosure principally concerns devices for assisting in placement of a needle or other percutaneously inserted medical device, tool or implement. In particular, the disclosure concerns embodiments of devices for providing safer and more accurate placement of such implements, for the safety and comfort of both patient and medical professional.

BACKGROUND

Various types of medical devices, including needles, access cannulas and similar tools are percutaneously inserted into the body, for a number of therapeutic, diagnostic or other purposes. In many cases, insertion of such devices are performed with the aid of imaging technology, such as x-ray fluoroscopy, magnetic resonance imaging, CT scanning, and the like. These technologies are employed in order to monitor passage of the device through the skin and/or other tissues to ensure the device passes along a desired path or is finally located properly after the process of insertion. For instance, a physician, technician or other professional can monitor fluoroscopic images at least periodically as the device is inserted or placed to compare the position(s) of the device to body tissues visible under the particular imaging technology. If the professional notes that the device is not at or moving toward a desired location, the professional can reorient the device or extract it and re-perform the insertion.

Using vertebroplasty procedures as a particular example, a clinician inserts a needle percutaneously to vertebra(e) to be treated. When the needle is determined to be in the proper place relative to a vertebra, e.g. by imaging technology such as those noted above, the needle is inserted into the vertebra and a support material (e.g. bone cement) is injected into the vertebra. The clinician is faced with several challenges in inserting and positioning the needle for proper access to the body of a vertebra. The generally preferred access is through either pedicle of the vertebra to be treated. One common access technique begins with the obtaining of an oblique fluoroscopic view of the patient that is perpendicular to the pedicles of the vertebra of interest. The clinician then aligns the longitudinal axis of the needle with that oblique view, and inserts the needle though the skin and soft tissues of the patient until the needle tip contacts the pedicle.

If the insertion is performed without further imaging, there is naturally a risk of misplacement of the needle, with the necessity of moving the needle or perhaps extracting it and placing it all over again. Under fluoroscopy, if the clinician manipulates the needle directly, his or her hands can be exposed to radiation at least to the extent that the needle's handle is in the beam of the imaging equipment. Further, in using imaging equipment, parts of the equipment (such as the C-arm of an x-ray machine) can be in the way of the clinician as he or she places the needle. To avoid exposure of the clinician's hands to radiation, it is known to position and align the vertebroplasty needle under imaging radiation using a remote handle or hemostats that grip the needle. The beam is then turned off and the clinician directs the needle based on the noted access point and alignment angle. However, the clinician's understanding or memory of the access point and alignment angle may not be as precise as is necessary, or may be altered as insertion begins or continues. Where a vertebroplasty needle is not correctly placed, generally it must be removed and placed again, using some or all of the noted steps. As such needles are generally large (e.g. 10 to 15 gauge) multiple attempts to place the needle on or adjacent a pedicle with the proper angle for entry of the needle into the pedicle can cause substantial extra trauma to the soft tissues of the back.

Consequently, accurate placement of a percutaneously-placed needle or other treatment device or implement can carry significant risk of radiation exposure for the clinician, while reducing that risk can raise the chance of an improper placement of the implement. There remains a need for devices and methods for use with percutaneously-placed implements to improve the accuracy of placement of the implement while minimizing patient discomfort and exposure of the medical professional to radiation.

SUMMARY

Among other things, there is disclosed embodiments of devices for assisting in aiming or guiding the insertion or other percutaneous use of a medical device. Particular embodiments of an aiming device for use in percutaneous placement of a medical device can include an elongated needle portion having a proximal portion and a distal portion, with the distal portion having a sharpened end. First and second directing members are fixed to the needle portion, and as an example the first directing member can be fixed to the proximal portion of the needle portion and the second directing member can be fixed to the needle portion at a position between the first directing member and the sharpened end. The directing members are spaced apart from each other by a distance and define a channel aligned along an axis that is parallel to the elongated needle portion. The first directing member in some embodiments at least partially defines a first space along the axis and forms at least part of the channel, and the distance separating the directing members is such that the entirety of the second directing member is viewable through the first space. It will be noted that the second directing member may also or alternatively be so configured. For example, the second directing member can at least partially define a second space along the axis and forming at least part of the channel, with that second space having a size and configuration allowing viewing of a body part through such first and second spaces when the aiming device is implanted in a body. At least one of the directing members may be of a material or configuration adapted to be visualized under a system for viewing internal bodily tissues. As an example, at least one of the directing members is of a radiopaque material to be easily visualized under fluoroscopy. As noted below, surfaces susceptible to visualization via ultrasound (echogenic surfaces), CT scans, magnetic resonance imaging or other imaging techniques can form part or all of one or both directing members.

In particular embodiments, a first directing member has a wall with a concave surface facing away from the needle portion. The concave surface may bound at least part of a first space that forms part of a channel, and the wall may have a thickness that is less than the diameter of the space. Similarly, a second directing member may have a wall at least partially bounding a second space. The distance separating the directing members can be such that the entirety of the second space is viewable through the first space along an axis through them. At least one of the first and second directing members is a closed ring in some embodiments, with the wall having a full-cylindrical internal surface that includes a concave surface facing away from the needle portion, and that defines the first space. Embodiments in which at least one of the first and second directing members is a C-shaped member, half-ring or part of a ring, having a wall with a concave surface facing away from the needle portion, are also disclosed.

As indicated above, embodiments of aiming devices can permit viewing or aiming through the directing members, with at least part of one of the directing members or a space it defines being viewable through the other. The distance between the directing members can help provide such a perspective. Accordingly, in particular embodiments the distance separating the directing members is between 20 and 50 percent of the length of the needle portion, for example about one-third or about 30 percent of the length of the needle portion.

One context for the use of embodiments of an aiming device as disclosed is in the medical procedure of vertebroplasty, as further discussed below. A vertebroplasty kit or set of devices can be provided, which include an aiming device as indicated herein along with devices for conducting vertebroplasty. For example, such a kit might include a vertebroplasty needle having an outer diameter adapted to pass through at least part of the channel of the aiming device. Other parts used in such procedures, such as a cement source, mixer, and/or syringe, may be included in such a kit or set.

The disclosure also concerns guides for use in percutaneous placement of a medical device in a patient's body. Examples of such guides can include an elongated mandrel portion having a proximal part and a distal part, with the distal part having a sharpened distal end and the mandrel portion having a longitudinal axis. First and second directing members are fixed to the mandrel portion. The first directing member is fixed to the proximal part of the mandrel portion and at least partially bounds a first space. The second directing member is fixed to the mandrel portion between the distal end and the first directing member, and it at least partially bounds a second space. A distance between the directing members is defined, and at least one of the directing members (e.g. the first directing member) includes or is made of a radiopaque material. The directing members are aligned with each other to define a channel that includes their first and second spaces and that is linear along a longitudinal axis parallel to the mandrel portion's longitudinal axis. The channel is sized and configured to accommodate at least a portion of the medical needle and allow it to travel along the channel. When viewed along the axis of the channel from a position proximal of the first directing member, at least a portion of the second directing member is visible through the first space of the first directing member.

Some embodiments may have the directing members the same or substantially identical in size and configuration. Examples of configurations for one or both of the directing members are closed ring(s) and C-shaped member(s). At least one of the spaces may be sized to accommodate and guide a portion of the medical device during the use of the medical device. In particular embodiments, the second space is substantially concentric with the first space when viewed along the second axis.

Methods for making and using aiming devices or guides are also disclosed. For example, a method can include inserting into a patient at a desired location a sharpened end of a guide having a mandrel with a longitudinal axis and that includes the sharpened end and a pair of directing members each defining a respective space lateral of the axis of the mandrel, with the directing members having a distance between one another and the spaces aligned along a second axis parallel to the longitudinal axis. An image is taken of the patient following the inserting, wherein the image is directed along the second axis through the spaces. It is determined whether a body portion of the patient where treatment is to be applied is within both of the spaces as seen in the image. If the body portion is not within both of the spaces as seen in the image, the inserting, taking and determining steps are repeated said until the body portion is so positioned. A medical device is inserted through the spaces and into the body portion of the patient where treatment is to be applied. The image may be taken using at least one of fluoroscopy apparatus, magnetic resonance imaging apparatus, CT scan apparatus, and ultrasound apparatus.

BRIEF DESCRIPTION OF THE DRAWINGS

FIG. 1 is a perspective view of an embodiment of a guiding device.

FIG. 1A is a close-up view of a portion of the embodiment of FIG. 1.

FIG. 2 is a side elevational view of the embodiment shown in FIG. 1.

DESCRIPTION OF THE ILLUSTRATED EMBODIMENTS

Figure 3:
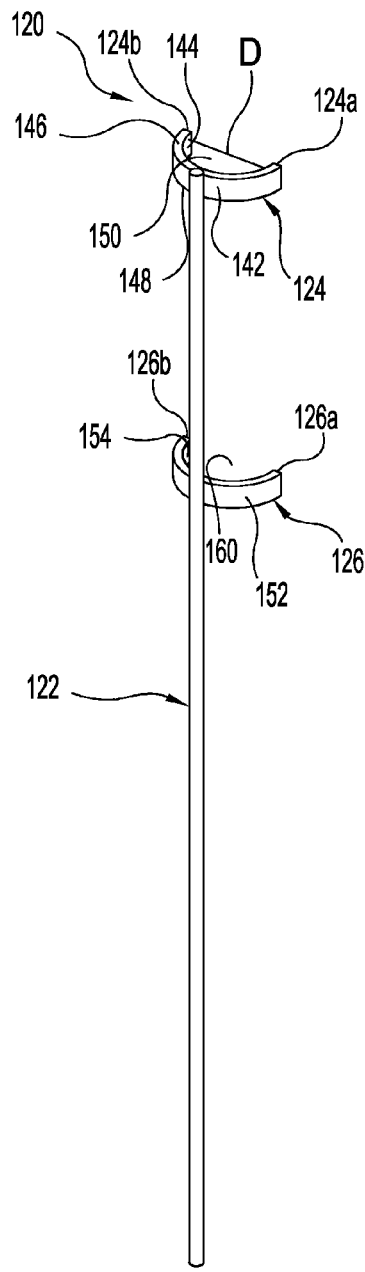
FIG. 3 is a perspective view of an embodiment of a guiding device.
Figure 4:
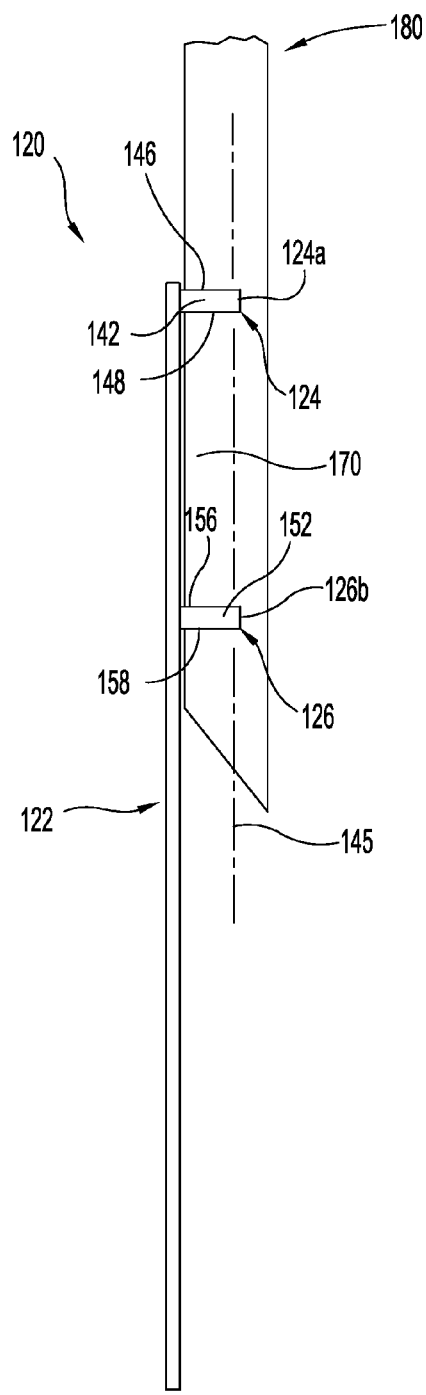
FIG. 4 is a side elevational view of the embodiment shown in FIG. 3.

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates.

Referring generally to the Figures, there are shown embodiments of a target needle or guiding device 20 useful in a number of medical applications for percutaneous placement of access, biopsy, therapeutic or other implements. While specific description with respect to a vertebroplasty or kyphoplasty procedure is made below, it will be understood that biopsy needles, cannulas or introducers for access to bone, organs, vessels and other body parts, and similar tools or implements can be used with embodiments or variants of guiding device 20.

Guiding or aiming device 20 includes an elongated needle portion 22 and one or more guiding or directing members. In the illustrated embodiments, two guiding members 24 and 26 are fixed to needle portion 22 with a defined space or distance 28 between them. In these embodiments, directing members 24, 26 do not move with respect to needle portion 28. In other embodiments, one or more of directing members 24, 26 may be fixed to needle portion 22 so as to be adjustable longitudinally, rotationally or pivotally with respect to needle portion 22.

Needle portion 22 is an elongated thin solid linear mandrel or shaft in the illustrated embodiment, having a substantially uniform circular-cylindrical shape. That structure and configuration provides for ease in insertion of needle portion 22 into the skin and/or other tissues in the body. It will be understood that other forms of needle portion 22 may be used. For example, a hollow tube could be used instead of a solid shaft for needle portion 22. Similarly, a non-cylindrical solid mandrel or shaft could be used, and if corners of such a shaft are deemed undesirable, such corners can be smoothed.

In a particular example, needle portion 22 includes a central mandrel portion 30, a proximal part or portion 32 having an end 34 and a distal part or portion 36 having an end or tip 38. Needle portion 22 is thin and linear in this embodiment, extending along a central longitudinal axis 39 from end to end. The diameter of needle portion 22 is uniform in this embodiment, and is substantially smaller than the device it is used to guide (e.g. a vertebroplasty needle, as discussed herein). As one example, needle portion 22 may be of 20 gauge, compared to 11 or 13 gauge needles and/or cannulas used with some vertebroplasty devices. The length of needle portion 22 measured from proximal end 34 to distal end 38 may depend on the type of medical treatment or process being done or the area of the body being accessed. For example, in vertebroplasty applications, needle portion 22 may have a preferred length of about 100 millimeters between ends 34 and 38 so that a sufficient part of needle portion 22 can be inserted into the patient to hold device 20 in place, as further described below. In the illustrated embodiments, distal end 38 is sharpened, as by providing a cut or beveled surface 40 that comes to a point 42 and forms a sharp edge 44. End 38 thus forms an insertion end that is relatively easily moved through skin and/or other tissue during use of guide 20.

Guiding or directing members 24 and 26 are fixed to needle portion 22, and are shown in particular embodiments in the drawings. Member 24 in this embodiment is a circular or substantially circular ring, having an outer perimetral surface 42 and an inner perimetral surface 44 each at a fixed distance from a central longitudinal axis 45. The length of surfaces 42 and 44 measured parallel to axis 45 is about five percent of the overall length of needle portion 22 in a particular example, i.e. about 5 millimeters when the overall length of needle portion 22 is about 100 millimeters. Planar surfaces 46 and 48 join and extend between surfaces 42 and 44, with the distance between surfaces 42 and 44 (i.e. the width of surfaces 46 and 48) being larger than the diameter of needle portion 22 and/or its mandrel portion 30 in the illustrated embodiments. The respective planes in which surfaces 46 and 48 exist are perpendicular to the central longitudinal axis 45 in this embodiment. Inner surface 44 defines a central space 50 and an inner diameter D that permits viewing or observation through it, and also permits guidance of another implement (e.g. a vertebroplasty needle), as will be explained further below.

In the embodiment of FIG. 1, directing member 26 is substantially identical to guiding member 24 in size and configuration, and is centered on axis 45 like member 24. Thus, directing member 26 is a circular or substantially circular ring, with outer perimetral surface 52 and an inner perimetral surface 54 each at a fixed distance from axis 45. Planar surfaces 56 and 58 join and extend between surfaces 52 and 54. The respective planes in which surfaces 56 and 58 exist are perpendicular to the central longitudinal axis 45 in this embodiment. Inner surface 54 defines a central space 60 and an inner diameter D similar or identical to the space and diameter noted above with respect to guiding member 24. Members 24 and 26 in this embodiment are made of a material that is radiopaque, e.g. biocompatible metals such as stainless steel, for visibility under fluoroscopy or other imaging techniques. In other embodiments, a portion (e.g. an outer shell or portion) may be of such a material, or materials particularly compatible with and visible under other types of imaging (e.g. ultrasound, CT scanning or magnetic resonance imaging) may be used. Thus, members 24, 26 may be constructed of thick-walled metal tubing, as one example.

As previously noted, each of guiding members 24 and 26 are fixed to needle portion 22, and in the illustrated embodiment the fixation is in both translation and rotation. That is, in these embodiments guiding members 24 and 26 are not movable along the length of needle portion 22, nor are they rotatable around axis 39 of needle portion 22. The illustrated embodiment shows guiding member 24 at or adjacent the proximal end 34 of needle portion 22, and in particular with its surface 46 substantially flush or even with end 34. Guiding member 26 in this embodiment is distally spaced from guiding member 24 at a position along needle portion 22. As a specific example, the distance between guiding members 24 and 26 may be about 30 percent of the total length of needle portion 22. Thus, in the example in which the length of needle portion 22 is 100 millimeters, the distance between guiding members 24 and 26 (e.g. between the centers of each, or the distance 28 between the facing planar surfaces of each) can be about 30 millimeters. Such a distance between members 24, 26 provides both separation to effectively guide a device moving along members 24, 26 and parallel to needle portion 22 (in this embodiment), and also to use in checking alignment of device 20 as discussed further below. It will be understood that other distances between guiding members 24 and 26, or other ratios of the distance between guiding members to the overall length of needle portion 22, can be used in other embodiments, particularly those that allow visualization through or along both guiding or directing members, and/or have a distance 28 between them that allows some or all of one directing member (e.g. member 26 or its space 60) to be seen in the central space of the other directing member (e.g. space 50 of member 24).

Figure 5:
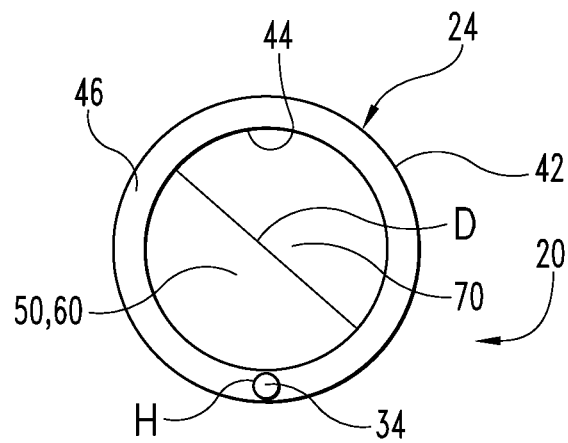
FIG. 5 is an end plan view of the embodiment shown in FIG. 1.
Figure 6:
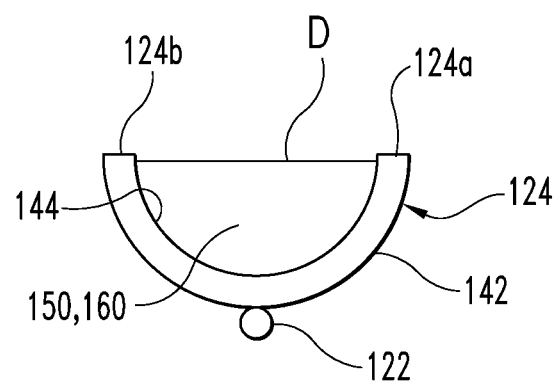
FIG. 6 is an end plan view of the embodiment shown in FIG. 3.

The fixation of guiding members 24, 26 to needle portion 22 can be accomplished in a number of ways. For example, each guiding member 24, 26 may include a hole or opening H in which a part of needle portion 22 is inserted. In such an embodiment, the fixation between guiding members 24, 26 may be a snap fit (e.g. tongue-and-groove or detent-type), an interference fit or press fit. Alternatively, adhesives, welding, soldering, brazing or other bonding techniques may be used to fix needle portion 22 within the respective holes H of guiding members 24, 26. Alternatively, guiding members 24, 26 may be fixed to needle portion 22 along respective portions of their outer surfaces 42, 52 (as in embodiments shown in FIGS. 3, 5 for example). Joining techniques such as welding, soldering, brazing, gluing or similar bonding can be used to fix guiding members 24, 26 to needle portion 22.

Directing members 24, 26 are positioned on needle portion 22 so that they are aligned with each other, with axis 45 through the centers of both spaces 50, 60. In such embodiments, if members 24, 26 are identical in shape and size, each point along one directing member has a corresponding point along the other directing member such that a line connecting those corresponding points is parallel to the axis of the needle portion and to the axis 45 of channel 70. These embodiments show internal surfaces 44, 54 of members 24, 26 are each cylindrical and forming a part of the same cylinder. As indicated above, surfaces 46, 48 of directing member 24 and surfaces 56, 58 of directing member 26 are generally each perpendicular to axis 45. With directing members 24, 26 so oriented, a lane or channel 70 is created that includes spaces 50, 60 defined by each guiding member 24, 26. In the illustrated embodiments, axis 45 along which channel 70 extends are parallel to axis 39 of needle portion 22.

One viewing directing members 24, 26 along axis 45 (and thus along channel 70) will thus see directing members 24, 26 at least substantially aligned with each other. The directing member closer to the viewer (e.g. member 24) will be seen in the foreground, and the directing member spaced from it (e.g. member 26) may be wholly hidden, or may be at least partly seen through the middle of the closer guiding member. For example, if the embodiment in FIG. 2 is viewed from a position along axis 45 and above member 24 (as seen in FIG. 2), then the viewer will see guiding member 24 in the foreground. Under observation by the naked eye, in some embodiments, guiding member 26 may be wholly or partly obscured by guiding member 24, or may be entirely viewable through space 50 in directing member 26. Under fluoroscopic or other imaging observation along axis 45, member 26 obscures member 24 because of their identical size and alignment in this embodiment, resulting in a view in which spaces 50, 60 coincide with each other. With viewing along axis 45, the spaces 50, 60 of guiding members 24, 26 in that embodiment are generally concentric with each other, and act as a sight to assist the clinician in aiming a device toward a desired location within the body. It will be understood that in other embodiments space 60 may be somewhat differently placed when viewed through space 50, for example off-centered with respect to space 60, or tangent or close to tangent with space 60.

As indicated above, directing members 24 and 26 are substantially identical in size and configuration in the illustrated embodiments. In other embodiments, member 26 and/or space 60 may be smaller than member 24 and/or space 50 so as to ensure viewing of part or all of space 60 within space 50. In some embodiments, space 60 of member 26 may be at least substantially concentric within and/or wholly overlapping space 50 of member 24 as viewed, or space 60 may be within or actually or approximately tangent to and within space 50 as viewed by the naked eye or imaging equipment. The distance between members 24 and 26 also provide spaced-apart guidance and/or support for a device to be inserted percutaneously into a patient, as will be described. If directing member 26 is somewhat smaller than directing member 24, it will be seen that more of directing member 26 will be viewable through directing member 26, and/or inner surface 54 of member 26 will appear to the viewer as closer to the center of space 50 of member 24.

Referring to FIG. 3, an embodiment of a device 120 that is similar to device 20 is shown, and features similar or identical to features discussed above are noted by the reference numbers given above with the prefix number 1. Needle portion 122 is identical to needle portion 22 in this embodiment. Directing members 124, 126 are partial rings, C-shaped and identical in shape and size, rather than full rings as in the embodiment of FIG. 1. Members 124, 126 are semi-circular or substantially semi-circular, subtending an arc between their respective ends 124a, 124b and 126a, 126b of about 180 degrees. It will be understood that such a C-shaped member 124 may have a larger (e.g. between 180 and 270 degrees) or smaller (e.g. between 90 and 180 degrees) subtended angle between its ends. Members 124, 126 in this embodiment each have respective outer perimetral surfaces 142, 152 and inner perimetral surfaces 144, 154, with each such surfaces at a fixed distance from a central longitudinal axis 145. Respective planar surfaces 146, 156 and 148, 158 join surfaces 142 and 144 are generally perpendicular to axis 145 and those perimetral surfaces and extend between their respective ends 124a, 124b and 126a, 126b. Inner surface 144 defines a central space 150 and inner surface 154 defines a central space 160, each of which is open as seen in the drawings, as opposed to the closed spaces 50, 60 of directing members 24, 26. Spaces 150, 160 form at least part of a lane or channel 170.

An inner dimension D is defined in spaces 150, 160 (seen with respect to member 124 in the drawings) that is sufficient for observation and/or guidance of another implement (e.g. a vertebroplasty needle) through channel 170, as will be explained further below.

While the illustrated embodiment demonstrates smoothly-curved guiding members 124, 126, it is to be understood that squared and/or generally U-shaped guiding members (e.g. having a linear base portion attached to needle portion 122 and lateral legs extending perpendicular to the base portion and in the same direction away from it) are also within the scope of this disclosure. Further, members 124, 126 are shown in the illustrated embodiment as attached to needle portion 122 along their respective outer perimetral surfaces 142, 152, as by brazing, welding, adhesive, or other ways of attaching. It will be understood that members 124, 126 may be attached to needle portion 122 in a similar way to that described above for members 24, 26 and needle portion 22, and vice versa.

An example of the use of guiding device 20 will now be given, in the context of placement and use of a vertebroplasty needle 80. It is to be understood that device 20 may be used in other contexts to assist with percutaneous placement of needles for other purposes, or for biopsy devices, implants, or other medical tools or devices.

Device 20 can be used both as an aiming device and as a guide for insertion of a medical device. In the vertebroplasty context, the clinician seeks to insert a needle into a vertebral body so that a supporting material, commonly a biocompatible cement, can be injected into a cavity within the vertebra. Accordingly, the clinician obtains a view of the vertebra(e) to be treated, as by known x-ray or other fluoroscopic imaging techniques. Vertebroplasty access is typically achieved through the pedicle of a vertebra, with a needle inserted through the pedicle to the interior of the vertebral body. Commonly an oblique fluoroscopic view of the pedicle is desirable.

After obtaining the desired view of the pedicle to be accessed, the clinician brings device 20 (e.g. sharpened tip 38) to a target skin location. The clinician can use a hemostat to bring device 20 to the location, particularly if a fluoroscopic or other imaging beam remains on, so as to reduce or eliminate exposure of the clinician's hand(s) to the fluoroscopic radiation. The target skin location is chosen so that needle portion 22 is directed at a point slightly to the side of the pedicle, or at a point on the pedicle where it is desired for the vertebroplasty needle 80 to penetrate the vertebra, so that axis 45 of device 20 is directed to that point for the vertebroplasty needle 80 to penetrate the vertebra. If fluoroscopic viewing of the patient is ongoing, use of a hemostat to grip device 20 (e.g. along mandrel portion 30, between end 38 and guiding member 26) and to insert or place it can keep the clinician's hands away from the beam.

Device 20 is then inserted into the patient's soft tissue (e.g. using the hemostat). The fluoroscope (e.g. the C-arm, encompassing an actual X-ray source and an image intensifier) may be adjusted to give an anterior-posterior view and/or a lateral view during the insertion if such additional views are needed or desired to properly position device 20. Insertion of device 20 continues at least until mandrel part 30 of needle portion 22 is within the patient to a sufficient degree to hold device 20 in a steady position or orientation relative to the patient's body. End 38 of needle portion 22 may contact the pedicle of interest or other bone tissue, if desired or appropriate. In particular embodiments, given the minimal weight of device 20, the sturdiness of needle portion 22, and the types of firm tissue device 20 is inserted into, about 10 percent of the length of needle portion 22 (e.g. about 10 millimeters in an embodiment as noted above) inserted into the body will suffice to maintain device 20 in place in the desired orientation.

With device 20 stably placed in the patient, the orientation of channel 70 of device 20 relative to the patient's vertebra of interest can be checked. A fluoroscopic view of the patient along axis 45 of channel 70 is observed. If device 20 is properly oriented and inserted, the fluoroscopic view will show directing members 24 and 26 aligned with each other and superimposed on the image of the vertebra, with the desired point for insertion of the vertebroplasty needle 80 on the pedicle (or other part of the vertebra) within the spaces 50, 60 of guiding members 24, 26. With directing members 24, 26 made of a radiopaque material, they act in a way similar to a firearm's sight when viewed under imaging (e.g. fluoroscopy). Thus, if the imaging (e.g. via fluoroscopy) shows that directing members 24 and 26 are aligned (e.g. with member 26 obscured by and disappearing behind member 24, or with one member shown at least partly within the other), yet the desired point on the pedicle is not within their spaces 50, 60, then channel 70 is not aimed at the desired point on the pedicle, and device 20 must be adjusted. If imaging shows directing members 24, 26 improperly oriented with respect to each other (e.g. with a portion of directing member 26 visible behind member 24, or a portion of space 60 outside of or not concentric with space 50 of directing member 24), then the C-arm of the fluoroscope (or other imaging device) can be re-oriented so that it directs the imaging view along axis 45 of channel 70 of device 20. An assessment of whether the point of interest on the pedicle is found within spaces 50, 60, as indicated above, can then be made to ensure that device 20 and its directing members 24, 26 direct channel 70 at that point of interest.

As indicated above, if the desired point for insertion of the vertebroplasty needle 80 is not within spaces 50, 60 of guiding members 24, 26, then device 20 is not properly oriented and/or is not in its proper position. It can then be moved, e.g. re-oriented or withdrawn and re-inserted to the proper location and/or orientation. Moving or placing device 20 over again is less traumatic to the patient than moving or re-placing a vertebroplasty needle 80 or other device of substantially larger diameter than needle portion 22.

Device 20 is properly located when the desired point of access to the vertebra of interest is observed within spaces 50 and 60 (e.g. substantially centered within one or both of spaces 50, 60), and therefore channel 70 along axis 45 points toward that desired point of access. When it is determined that device 20 is so located, any remaining radiation for imaging can be turned off. The clinician can use device 20 to guide the vertebroplasty needle 80 during insertion. Channel 70 defined by directing members 24, 26 are known (through the above process) to be directed to the desired point on the vertebra or pedicle for insertion of the vertebroplasty needle 80. The clinician moves the vertebroplasty needle 80 through channel 70 (i.e. through or along spaces 50, 60 of directing members 24, 26, or against or adjacent the inner concave surfaces of guiding members 124, 126). Using directing members 24, 26 of device 20 as physical guides or supports, the vertebroplasty needle 80 is inserted through the patient's skin and into the vertebra to be treated. If desired, a cannula, tube or introducer may be placed first into the patient using channel 70 as a guide, and the vertebroplasty needle 80 can be inserted through such a cannula or introducer. Once the vertebroplasty needle 80 has been inserted into the vertebra, the clinician can remove device 20 from the patient's body, or he or she can allow it to remain as a support or guide during the injection phase of the vertebroplasty procedure.

When the injection has been completed, the vertebroplasty needle 80 is withdrawn from the patient. If device 20 has remained in place in the patient throughout the injection, the vertebroplasty needle 80 can be withdrawn along channel 70, e.g. through spaces 50, 60 of device 20. In that case, device 20 helps to keep the needle along its insertion orientation, so that minimal stress or injury to the soft tissues from the needle results. If an embodiment similar to that of device 120 of FIG. 3 is used, a vertebroplasty needle 180 or other tool or device has somewhat more freedom in removal because of the open nature of guiding members 124, 126 and their spaces 150, 160 forming part of channel 170. If not removed previously, device 20 is also withdrawn from the patient. The procedure using device 20 can be repeated with respect to another vertebra, or with respect to the same vertebra in a different location on that vertebra, as may be medically necessary or desirable. It will be understood that multiple devices 20 may be inserted as indicated above for a vertebroplasty procedure treating multiple vertebrae or locations on a vertebra, rather than placing one or more devices 20 sequentially.

Device 20 thus gives a radiologically visible sight or indicator as to where the larger vertebroplasty needle 80 will travel within the patient if passed along channel 70, and is stable enough when inserted in the patient to keep its position without being held in place by the clinician or a piece of equipment. When device 20 is in contact with or adjacent the vertebra, the clinician can check that guiding members 24, 26 are aligned in a (oblique) radiological view and centered on the targeted portion of the vertebra/pedicle. The thin needle portion 22 (compared to a width of a vertebroplasty needle) enters the tissue with less resistance, and can be oriented or re-oriented with greater ease and less trauma, than such a relatively large needle, tool or implant. Fluoroscopy may then be discontinued, and device 20 provides a guide channel 70 for the entry of the vertebroplasty needle 80 though guiding members 24, 26. The clinician is then free to insert the vertebroplasty needle 80 though soft tissue and though the pedicle without the use of fluoroscopy, reducing radiation exposure to the clinician (and perhaps to a lesser extent, the patient), and also allows the clinician to position their hands and body more conveniently for the vertebroplasty procedure without the imaging equipment being in the way.

It will be noted that needle portion 22 and its central mandrel portion 30, being a thin body, may easily be gripped firmly by one or more haemostats. Larger vertebroplasty needles are more likely to slip out of the haemostats, and may prevent the haemostat(s) from being locked closed. Also, the target needle is very light in weight in particular embodiments so as to be self-supporting after relatively minimal access though soft tissue (e.g. about 1 to 2 centimeters). This allows the clinician to release the haemostat(s) used to hold and insert device 20, and to use both hands for other functions. For example, the clinician can rotate at least a portion of his or her imaging equipment (e.g. the C-arm of a fluoroscope) through other views to obtain a different, optimal or necessary angle of alignment. Device 20 provides an indicator to show where the vertebroplasty needle 80 or other device will arrive or enter inside the vertebral body, and how it is or will be oriented, in these images.

As noted in the vertebroplasty example given above, x-ray or fluoroscopy is described as an imaging technique that can be used with device 20 to aim it and guide a vertebroplasty needle 80 to a desired location. In that case, one or both of directing members 24 and 26 may be made of or include radiopaque materials. Where both directing members 24 and 26 are so fashioned, both members will be visible on a fluoroscopic image, along with a vertebra or pedicle, and the clinician can ensure that members 24, 26 and the desired point on the bone are properly aligned. It will be understood that embodiments of device 20 can be made for use with one or more other functions, such as ultrasound, CT scanning, and magnetic resonance imaging. In such embodiments, it may be preferred to form or provide members 24, 26 with materials, configurations or other attributes that effectively reflect energy used in such technologies, or otherwise ensure that members 24, 26 appear on such images.

The size and shape of spaces 50, 60 of members 24, 26 may be made with one or more particular uses of device 20 in mind. For example, in the vertebroplasty example given above, spaces 50 and 60 (and channel 70 of which they are part) may be sized and configured so that a vertebroplasty needle 80 fits easily and can slide along them. For a 15 gauge vertebroplasty needle, the diameter of spaces 50 and 60 may be slightly larger than 15 gauge, and substantially cylindrical. The distance between the axis 45 of channel 70 and axis 39 of needle portion 22 is thus slightly larger than the radius of the vertebroplasty needle. Of course, embodiments of device 20, 120 can be made with other sizes or configurations for use in aiming or guiding insertion of other types of access or treatment devices or implants.

Further, while the embodiments of device 20, 120 discussed above include those in which two guiding members 24, 26, 124, 126 are attached to one needle portion 22, 122, it will be understood that other configurations are also contemplated. For instance, embodiments having two or more needle portions 22, 122 attached to guiding member(s) as discussed above are envisaged. In particular embodiments, multiple needle portions 22, 122 may be evenly spaced from each other, may be diametrically opposed to each other, may be grouped together, and/or in other configurations. Multiple needle portions may provide additional stability, if necessary, in placing device 20, 120 stably in soft tissue, and in holding the guiding member(s) steady during use. Similarly, as noted previously a single guiding member or more than two such guiding members may be used in a single device 20, 120, and guiding members of different configurations may be used in a single device 20, 120. For example, devices having one or more guiding members 24 and one or more guiding members 124 aligned as indicated above are contemplated.

Thus, exemplary embodiments of the guiding or aiming device can include a thin solid mandrel to minimize trauma to the patient and to be easily adjusted to be perpendicular to fluoroscopy or other imaging. A set of spaced rings in or near the top or proximal end of the mandrel or needle portion (e.g. located at or up to 3 to 4 centimeters from the top) show where a device (e.g. the center of a vertebroplasty needle) will travel. The mandrel is inserted remotely (e.g. via hemostats) into the soft tissue. The thin needle or mandrel and its rings or other guiding or directing members give a visual marker to where the larger vertebroplasty needle 80 or other device will travel and once in the patient is stable enough to keep its position without being held in place. Once the mandrel portion is inserted into the patient and is in contact with the vertebra or close to it the clinician can check that the directing members (like ghost rings of a firearm sight) are aligned and centered on the targeted portion of the tissue of interest, such as a pedicle or other portion of a vertebra. Fluoroscopy may be discontinued and the target needle now provides a guide for insertion of a medical device though the rings.

An exemplary procedure utilizes the guiding or aiming device for targeting and establishing the proper angle that will subsequently be used to insert a treatment or other medical device. The mandrel or needle portion of the directing device, being thin and solid in particular examples, may easily be gripped firmly and inserted into tissue by hemostat(s). This allows the clinician to release the hemostat(s) and use both hands for other functions, such as allowing repositioning of a fluoroscope C-arm or other imaging device to or through other views to insure a desirable or optimal angle to a target internal location is achieved. The clinician uses the guiding or directing members (e.g. rings or part-rings) as sights to align the aiming device perpendicular to the (fluoroscopic) image. Once successful placement of the aiming device is confirmed the clinician may then use the rings to align the treatment device or implant to be inserted parallel with the mandrel or needle portion of the aiming device. The clinician is now free to push the treatment device or implant into the body (e.g. through soft tissue and a pedicle) without the use of fluoroscopy.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected. It is to be understood that structures or embodiments described in one context or with respect to one component may be used in other contexts or with respect to other components.

What is claimed is:

1. An aiming device for use in percutaneous placement of a medical device, comprising:
   a one-piece non-hollow needle portion having a proximal portion and a distal portion, said distal portion having a sharpened end;
   first and second directing members fixed to said needle portion, said first directing member being fixed at a proximal end of said needle portion and said second directing member being fixed to said needle portion at a position between said first directing member and said sharpened end, said directing members being non-rotatable with respect to said sharpened end;
   wherein said directing members are spaced apart from each other by a distance and define a channel aligned along an axis that is parallel to said one-piece non-hollow needle portion, and wherein at least one of said directing members includes an inner perimetral surface having a first constant distance from said axis and an outer perimetral surface having a second constant distance from said axis and a uniform width that is the difference between said first and second constant distances, and wherein the needle portion has an outer diameter that is less than or equal to said uniform width.

2. The aiming device of claim 1, wherein said first directing member at least partially defines a first space along said axis and forming at least part of said channel, and said distance is such that the entirety of said second directing member is viewable through said first space.

3. The aiming device of claim 2, wherein said second directing member at least partially defines a second space along said axis and forming at least part of said channel, said second space having a size and configuration allowing viewing of a body part through said first and second spaces when said aiming device is implanted in a body.

4. The aiming device of claim 3, wherein at least one of said directing members is of a material or configuration adapted to be visualized under a system for viewing internal tissues.

5. The aiming device of claim 4, wherein at least one of said directing members is of a radiopaque material to be easily visualized under fluoroscopy.

6. The aiming device of claim 1, wherein said first directing member has a wall with a concave surface facing away from said needle portion, said concave surface bounding at least part of a first space, said first space forming part of said channel, said wall having a thickness that is less than the diameter of said space.

7. The aiming device of claim 6, wherein said second directing member has a wall at least partially bounding a second space, and said distance is such that the entirety of said second space is viewable through said first space along said axis.

8. The aiming device of claim 7, wherein at least one of said first and second directing members is a closed ring, said wall having a full-cylindrical internal surface that includes said concave surface facing away from said needle portion, and that defines said first space.

9. The aiming device of claim 7, wherein at least one of said first and second directing members is a C-shaped member having said wall with a concave surface facing away from said needle portion.

10. The aiming device of claim 7, wherein said distance is between 20 and 50 percent of the length of said needle portion.

11. The aiming device of claim 10, wherein said distance is about 30 percent of the length of said needle portion.

12. The aiming device of claim 1, wherein said directing members are the same in size and configuration.

13. The aiming device of claim 1, wherein at least one of said directing members is a closed ring.

14. The aiming device of claim 1, wherein at least one of said directing members is a C-shaped member.

15. The aiming device of claim 1, wherein at least one of said directing members is sized to accommodate and guide a portion of the medical device during the use of the medical device.

16. The aiming device of claim 1, wherein said second space is substantially concentric with said first space when viewed along said second axis.

17. The aiming device of claim 1, wherein said second directing member is fixed to said elongated needle portion on the proximal half of said elongated needle portion.

18. The aiming device of claim 1, wherein said distal portion of said elongated needle portion that extends distally beyond said second directing member defines a cylinder of substantially constant diameter, except for said sharpened end.

19. The aiming device of claim 1, wherein said needle portion passes through at least one of said directing members between said inner and outer perimetral surfaces.

20. A vertebroplasty kit, comprising:
an aiming device for use in percutaneous placement of a medical device including a one-piece non-hollow needle portion having a proximal portion and a distal portion said distal portion having a sharpened end, and first and second directing members fixed to said needle portion, said first directing member being fixed at a proximal end of said needle portion and said second directing member being fixed to said needle portion at a position between said first directing member and said sharpened end, said directing members being non-rotatable with respect to said sharpened end, and wherein said directing members are spaced apart from each other by a distance and define a channel aligned along an axis that is parallel to said one-piece non-hollow needle portion; and
a vertebroplasty needle having an outer diameter adapted to pass through at least part of said channel.

\* \* \* \* \*